(12) United States Patent
Hirata et al.

(10) Patent No.: US 7,601,878 B2
(45) Date of Patent: Oct. 13, 2009

(54) PROCESS AND UNIT FOR PRODUCTION OF PERFLUOROALKYL IODIDE TELOMERS

(75) Inventors: Tatsuya Hirata, Settsu (JP); Kouzou Noda, Settsu (JP); Jun Miki, Settsu (JP)

(73) Assignee: Daikin Industries, Ltd., Osaka (JP)

( * ) Notice: Subject to any disclaimer, the term of this patent is extended or adjusted under 35 U.S.C. 154(b) by 0 days.

(21) Appl. No.: 11/723,115

(22) Filed: Mar. 16, 2007

(65) Prior Publication Data

US 2007/0161831 A1   Jul. 12, 2007

Related U.S. Application Data

(62) Division of application No. 10/493,379, filed as application No. PCT/JP02/10872 on Oct. 21, 2002.

(30) Foreign Application Priority Data

Oct. 24, 2001   (JP)   ............... P2001-326555

(51) Int. Cl.
  *C07C 17/38*   (2006.01)
  *C07C 17/269*   (2006.01)
  *C07C 17/278*   (2006.01)

(52) U.S. Cl. .................. 570/139; 502/21; 570/126; 570/138; 570/172; 570/182

(58) Field of Classification Search ............... 570/182, 570/126.172, 138, 139; 502/21
See application file for complete search history.

(56) References Cited

U.S. PATENT DOCUMENTS

| | | | |
|---|---|---|---|
| 3,071,614 A * | 1/1963 | Knobloch | 562/485 |
| 3,429,901 A | 2/1969 | Blood et al. | |
| 3,817,856 A * | 6/1974 | Aaron et al. | 208/213 |
| 3,883,604 A * | 5/1975 | Rudolph et al. | 570/139 |
| 3,933,931 A | 1/1976 | Oda et al. | |
| 4,160,113 A * | 7/1979 | Muller et al. | 568/772 |
| 4,482,750 A * | 11/1984 | Hetzel et al. | 568/621 |
| 4,525,267 A * | 6/1985 | Inooka | 208/58 |
| 4,849,556 A | 7/1989 | Dannels et al. | |
| 5,068,471 A * | 11/1991 | Paul et al. | 570/139 |
| 5,268,516 A * | 12/1993 | Bertocchio et al. | 570/139 |
| 5,294,329 A | 3/1994 | Kramer | |
| 5,304,522 A | 4/1994 | Jalkian et al. | |
| 5,395,997 A | 3/1995 | Van Der Puy et al. | |
| 5,639,923 A | 6/1997 | Von Werner | |
| 5,650,545 A * | 7/1997 | Bertocchio et al. | 570/172 |
| 5,792,893 A | 8/1998 | Wilson et al. | |
| 5,900,159 A | 5/1999 | Engel et al. | |
| 5,929,292 A * | 7/1999 | Shimoyama et al. | 568/842 |
| 6,369,285 B1 | 4/2002 | Mathieu et al. | |
| 6,399,839 B1 | 6/2002 | Mathieu et al. | |
| 6,399,840 B1 | 6/2002 | Schoebrechts et al. | |
| 6,441,256 B1 | 8/2002 | Mathieu et al. | |
| 6,452,057 B1 | 9/2002 | Lambert et al. | |
| 6,730,817 B1 | 5/2004 | Wilmet et al. | |
| 6,919,490 B2 * | 7/2005 | Funakoshi et al. | 570/172 |
| 7,030,286 B2 | 4/2006 | Rottger et al. | |
| 7,112,709 B2 * | 9/2006 | Klausmeyer | 570/216 |
| 7,214,815 B2 | 5/2007 | Funakoshi et al. | |
| 2005/0049443 A1 | 3/2005 | Wilson | |
| 2005/0234281 A1 | 10/2005 | Bjorklund et al. | |
| 2007/0161831 A1 | 7/2007 | Hirata et al. | |

FOREIGN PATENT DOCUMENTS

| | | | |
|---|---|---|---|
| DE | EP 718262 A 1 | * | 6/1996 |
| JP | 47-2869 | | 2/1972 |
| JP | 51-41332 | | 4/1976 |
| JP | 61-120641 A | | 6/1986 |
| JP | 8-239336 A | | 9/1996 |
| JP | 10-113551 A | | 5/1998 |
| JP | 11-286457 A | | 10/1999 |
| JP | 2000-506061 A | | 5/2000 |
| WO | WO 97/31693 A | | 9/1997 |

OTHER PUBLICATIONS

Chen et al., "Copper-Induced Telomerization of Tetrafluoroethylene With Fluoroalkyl Iodides," Journal of Fluorine Chemistry 36 (1987) pp. 483-489.
Top Fluorochem Co, Ltd. Fluoro Telomers, 2009, Abstract, 4 pages.

* cited by examiner

*Primary Examiner*—Peter G O'Sullivan
(74) *Attorney, Agent, or Firm*—Birch, Stewart, Kolasch & Birch, LLP

(57) ABSTRACT

A solid catalyst used in, for example, production of a perfluoroalkyl iodide telomer is effectively and continuously recovered and the recovered catalyst is continuously recycled to the reactor for reuse. A slurry containing a reaction product and the catalyst is drawn from the reaction system, and the catalyst in the drawn slurry is classified by means of a hydrocyclone, whereby a high-concentration slurry whose catalyst concentration is higher than that of the drawn slurry and a low-concentration slurry whose catalyst concentration is lower than that of the drawn slurry are obtained, and the high-concentration slurry is recycled to the reaction system.

6 Claims, 1 Drawing Sheet

PROCESS AND UNIT FOR PRODUCTION OF PERFLUOROALKYL IODIDE TELOMERS

This application is a Divisional of co-pending application Ser. No. 10/493,379 filed on Apr. 22, 2004, and for which priority is claimed under 35 U.S.C. § 120. Application Ser. No. 10/493,379 is the national phase of PCT International Application No. PCT/JP02/10872 filed on Oct. 21, 2002, under 35 U.S.C. § 371. Priority is claimed under 35 U.S.C. § 120 for applications Ser. No. 10/493,379 PCT/JP02/10872. This application claims priority under 35 U.S.C. § 119 to Japanese application no. 2001-326555, filed on Oct. 24, 2001. The entire contents of each of the above-identified applications are hereby incorporated by reference.

TECHNICAL FIELD

The present invention is related to a method and a system for recovering a catalyst which has been used in a chemical reaction, and to a method and an apparatus for producing a perfluoroalkyl iodide telomer wherein the recovery method is employed.

BACKGROUND ART

A catalyst is used in various chemical reactions. Generally, the catalyst is recovered from a reaction mixture containing a reaction product and recycled to the reaction system in an industrial plant. The main purpose of the recovery and recycle of the catalyst is to reduce costs.

A telomerization reaction of perfluoroalkyl iodide with tetrafluoroethylene is one of the chemical reactions wherein recovery and recycle of a catalyst are carried out. The perfluoroalkyl iodide telomers obtained by the telomerization reaction are useful chemicals as a material for a surfactant or a water- and oil-repellant applied to fiber.

There is disclosed that copper powder is used as a catalyst for the telomerization reaction in "Copper-Induced Telomerization of Tetrafluoroethylene with Fluoroalkyl Iodides", Chen et al., Journal of Fluorine Chemistry 36 (1987), pp. 483 to 489. The advantage of the telomerization reaction which employs copper powder is that the reaction proceeds at a relatively low temperature between 80 and 100° C., and that a shorter reaction time is required to accomplish a certain result compared with a telomerization reaction wherein an organic peroxide is used as a catalyst.

The copper catalyst which has been used in the telomerization reaction is recovered by, for example, drawing a reaction mixture from a reactor and carrying out a solid-liquid separation operation outside the reactor. The "reaction mixture" means a mixture which contains a catalyst in a solid phase and a reaction product in a liquid phase, and may further include an unreacted starting material. The recovered catalyst is mixed with the starting material and so on and recycled to the reactor for reuse. It is difficult to continuously carry out this catalyst recovery and recycle method since the method accompanies complicated operations.

The inventors of the present invention have studied the applicability of an apparatus which is disclosed in Japanese Laid-Open (Kokai) Publication No. 11-286457 (1999) to the telomerization reaction. That is, the inventors have studied the possibility of using an apparatus wherein a filter is immersed in the reaction fluid which includes the catalyst and the perfluoroalkyl iodide telomers obtained by the telomerization reaction. The filter is a porous filter such as a sintered metal filter. This apparatus enables the telomerization reaction and the catalyst recovery to be conducted simultaneously. Conducting a chemical reaction (for example, the telomerization reaction) "continuously" means withdrawing a reaction product while introducing a starting material into a reactor without interrupting the chemical reaction.

In this apparatus, the reaction fluid containing the catalyst reaches a surface of the filter by being stirred with a stirrer. Next, only the liquid phase of the reaction fluid passes through the filter and into the inside of the filter, whereby the catalyst particles are left on the filter surface. The liquid phase (containing a reaction product) which does not contain the catalyst is delivered to the outside of the reactor via a conduit which communicate with the filter. The catalyst on the filter surface are returned to the reaction fluid by being scratched from the filter surface by force exerted by the stirred fluid. The telomerization reaction can be carried out continuously by feeding the starting material into the reactor continuously while conducting the filtration and scratching.

DISCLOSURE OF INVENTION

The apparatus as described above which has a filter disposed in the reactor is useful for producing telomers continuously. However, even if the catalyst is scratched from the filter surface by using the force of the stirred fluid, the catalyst accumulates little by little on and within the filter, whereby plugging of the filter is inevitably caused. For this reason, when operating the apparatus for long period, the pressure loss caused by the filter plugging is increased, which makes it difficult to draw the product from the reactor and thereby the continuous telomer production is obstructed.

In light of this situation, the object of the present invention is to provide a method for recovering a catalyst, which method enables a chemical reaction using a catalyst (such as a telomerization reaction) to proceed continuously, and a method and a system for producing a perfluoroalkyl iodide telomer wherein the recovery method is employed.

In order to achieve the above-mentioned object, the present invention provides a method for recovering a catalyst which has been used for a chemical reaction, which comprises:

drawing a slurry containing a reaction product in a liquid phase and the catalyst in a solid phase from a reaction system; and classifying the catalyst in the drawn slurry by means of a centrifugal classifier to give a high-concentration slurry having a catalyst concentration higher than that of the drawn slurry.

The method for recovering a catalyst of the present invention is characterized by using a centrifugal force for the purpose of recovering the catalyst from the slurry containing the catalyst. That is, the method for recovering a catalyst of the present invention is a method for recovering a catalyst in the form of slurry that has a higher content of catalyst, which method includes obtaining two slurries from a slurry containing a reaction product in a liquid phase and a catalyst in a solid phase, one obtained slurry having a lower content of catalyst and the other obtained slurry having a higher content of catalyst, and the latter being recovered.

The slurry drawn from the reaction system contains the reaction product that is an objective material and the catalyst and may further contains unreacted starting materials and by-product. In this slurry, the specific gravity of the catalyst which is a solid phase is larger than that of the liquid phase. In this slurry, the solid phase is substantially comprised of the slurry, and therefore the concentration of catalyst (or the content of catalyst) in the slurry corresponds to the slurry concentration which means the concentration of the solid phase (that is, the suspensoid).

The centrifugal classifier which is used in the present invention is a classifier which produces a) a high-concentration slurry whose slurry concentration (that is, the catalyst concentration) is higher than that of the slurry which is supplied to the classifier (in this specification, such a slurry is merely referred to as a "high-concentration slurry" or "heavy liquid"), and b) a low-concentration slurry whose slurry concentration is lower than that of the slurry which is supplied to the classifier (in this specification, such a slurry is merely referred to as a "low-concentration slurry" or "light liquid"). The classifier is a device for separating particles in the slurry into a group of particles whose diameter is larger than classification point and a group of particles whose diameter is smaller than the classification point. Therefore, in general, the high-concentration slurry contains course particles and the low-concentration slurry contains fine particles. When all the particles in the slurry that is supplied to the classifier have the same particle diameter, substantially all the particles are contained in the high-concentration slurry and "separated" from the slurry supplied to the classifier.

In the method for recovering a catalyst of the present invention, the catalyst is recovered in the form of high-concentration slurry. The low-concentration slurry containing the reaction product is delivered to the next step. Specifically, the next step is a step of further separating the catalyst in the low-concentration slurry by means of a centrifugal classifier, or taking the reaction product out of the low-concentration slurry.

According to the method for recovering a catalyst, from the slurry containing the reaction product, the catalyst can be recovered in the form of slurry at a high recovery percentage. The catalyst recovered in the form of slurry may be continuously recycled to the reaction system via a conduit. Further, in the case where the catalyst is continuously drawn and subjected to a classification process followed by being recycled to the reaction system via a conduit, the possibility of exposing the catalyst to the outside air is eliminated or reduced, whereby the deactivation of the metal catalyst due to the surface oxidation is reduced. Thus, this recovery method gives an advantage that the activity of the recovered is high, that is, the degree of deactivation is small. There is also an advantage that the amount of loss is reduced by recycling the recovered catalyst to the reaction system continuously.

The centrifugal classifier used in the present invention is a wet type centrifugal classifier, such as a centrifugal settling machine or a hydrocyclone. In the present invention, the hydrocyclone is particularly preferably used because the continuous running thereof is easily conducted. In the case where the hydrocyclone is used, the high-concentration slurry is discharged from the bottom outlet and the low-concentration slurry is discharged through an overflow riser tube.

The method for recovering a catalyst of the present invention is applied to a chemical reaction wherein the reaction product is a liquid phase and a catalyst is a solid phase. The method for recovering a catalyst of the present invention is preferably applied to a telomerization reaction of a perfluoroalkyl iodide with tetrafluoroethylene, wherein copper particles are used as the catalyst.

The present invention also provides a system for recovering a catalyst, which includes:

a hydraulic classifier;

a line which is connected to a reactor and through which a slurry containing a reaction product in a liquid phase and the catalyst in a solid phase, that is, a reaction mixture is delivered from the reactor to the hydraulic classifier; and a line through which a high-concentration slurry is delivered to the reactor. The high-concentration slurry is obtained by classifying the catalyst contained in the slurry from the reactor, with use of the classifier. This system is a system for carrying out the catalysts recovery method of the present invention, and the effect of this system is the same as that of the catalyst recovery method of the present invention. Therefore, by using this system with a reactor, it is possible to construct an industrial plant wherein the catalyst is continuously recovered and recycled to the reaction system.

In this recovery system, the line is specifically a pipe. The pipe may be rigid or flexible. The hydraulic classifier is preferably a hydrocyclone. In this recovery system, a plurality of hydrocyclones are connected in series or parallel, as described below.

The present invention also provides a method for producing a method for producing a perfluoroalkyl iodide telomer by a telomerization reaction of a perfluoroalkyl iodide with tetrafluoroethylene catalyzed with a solid catalyst, which includes:

drawing a slurry containing the perfluoroalkyl iodide telomer and the catalyst from a reaction system;

classifying the catalyst in the drawn slurry by a centrifugal classifier to give a high-concentration slurry whose catalyst concentration is higher than that of the drawn slurry and a low-concentration slurry whose catalyst concentration is lower than that of the drawn slurry; and recycling the high-concentration slurry to the reaction system.

This production method is characterized by that a catalyst is recovered in the form of high-concentration slurry (that is, a heavy liquid) and then recycled to the reaction system by using the catalyst recovery method of the present invention. In this production method, the reaction product which is the perfluoroalkyl iodide telomer is drawn from the hydraulic classifier in the form of low-concentration slurry and subjected to the next step. The next step is specifically a step of separating the catalyst contained in the low-concentration slurry with the use of a centrifugal classifier and so on, or a step of taking the telomer out of the low-concentration slurry.

According to this production method, it is possible to continuously recover the catalyst and recycle it to the reaction system by continuously drawing the slurry from the reaction system and delivering the slurry to the centrifugal classifier. Therefore, it is possible to recover and reuse the catalyst continuously while producing the perfluoroalkyl iodide telomer continuously by feeding starting materials to the reaction system continuously so that the telomer is synthesized continuously in an amount which corresponds to an amount of the telomer contained in the slurry drawn from the reaction system. Further, as described above, the loss and the degree of deactivation of the recovered catalyst can be reduced by recycling the catalyst to the reaction system continuously, and therefore, the telomer of constant quality can be continuously produced for long period of time.

In the method for producing a perfluoroalkyl iodide telomer of the present invention, the catalyst is preferably copper particles. The reason therefore is as described in the prior art.

In the method for producing a perfluoroalkyl iodide telomer of the present invention, the catalyst is preferably classified by the centrifugal classifier so that 90% by weight of the catalyst is distributed to the high-concentration slurry (that is, the heavy liquid). The expression "90% by weight of the catalyst is distributed to the high-concentration slurry" means that the weight ratio of the catalyst contained in a discharge per unit time of the high-concentration slurry is at least 90% of the total weight of the catalyst contained in a discharge per unit time of the low-concentration slurry and the discharge per unit time of the high-concentration slurry. As the ratio of the catalyst distributed in the high-concentration slurry is smaller, the recovery percentage is smaller, which is disadvantageous in terms of cost.

In the method for producing a perfluoroalkyl iodide telomer of the present invention, the concentration of the catalyst in the reaction system is preferably constant in order to carry out the telomerization reaction stably. In order to achieve the constant concentration of the catalyst in the reaction system, a fresh catalyst may be added to the reaction system, if necessary.

The present invention also provides an apparatus for carrying out the method for producing a perfluoroalkyl iodide telomer of the present invention, which includes:

a reactor;

a hydraulic classifier;

a line which is connected to the reactor and through which a slurry containing the pertluoroalkyl iodide telomer and a catalyst is delivered from the reactor to the hydraulic classifier; and a line through which a high-concentration slurry is delivered to the reactor. The high-concentration slurry is obtained by classifying the catalyst contained in the slurry from the reactor, with use of the classifier.

This apparatus includes a reactor wherein the telomerization reaction proceeds and the system for recovering a catalyst of the present invention. By using this production apparatus, it is possible to synthesize the perfluoroalkyl iodide telomer continuously while recovering the catalyst and recycling it to the reaction system continuously.

Figure 1:
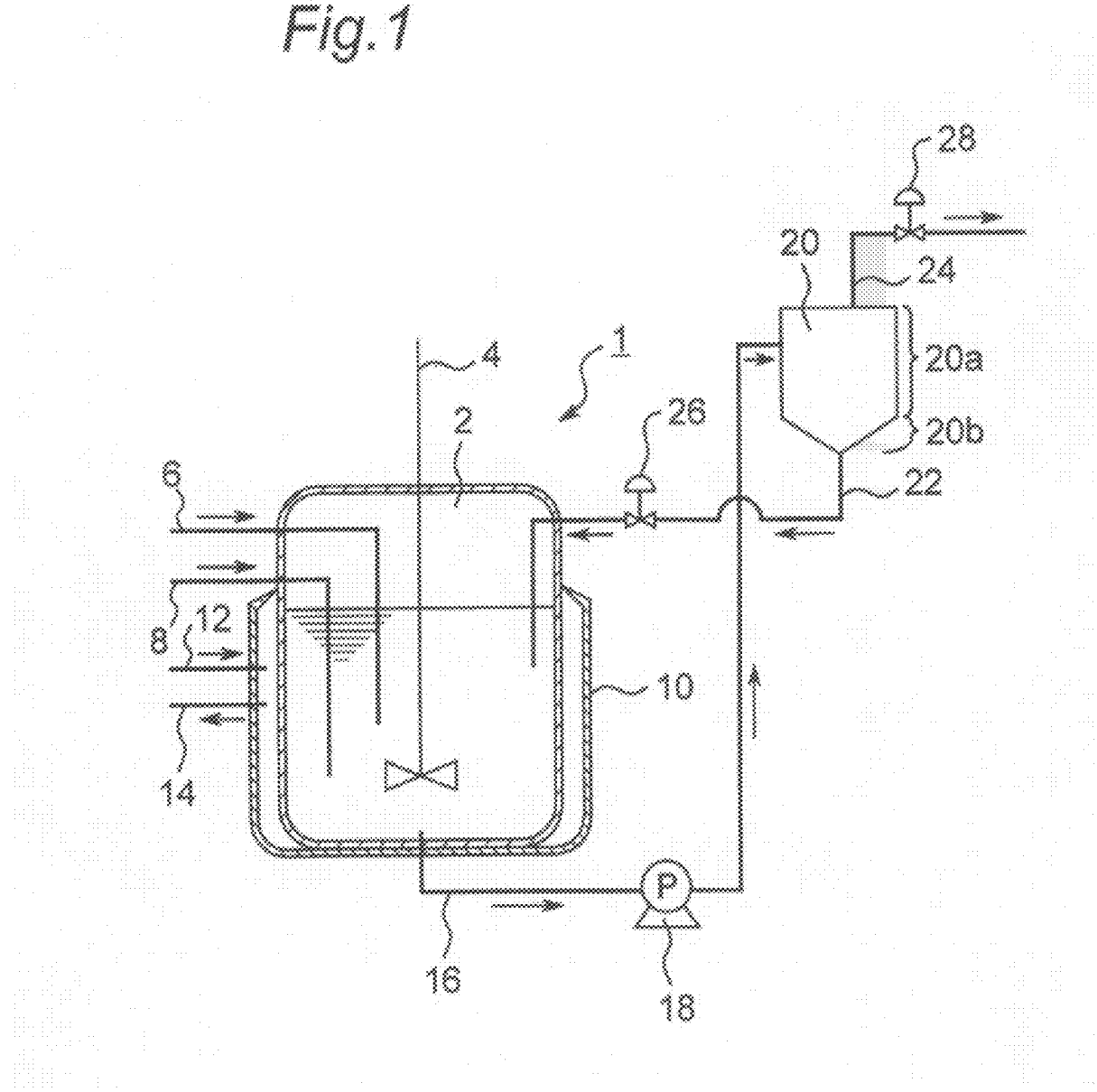
FIG. 1 shows a schematic view of an embodiment of an apparatus for producing a perfluoroalkyl iodide telomer of the present invention.

In the drawing, the reference numerals denote the following elements:

1 . . . telomer production apparatus; 2 . . . reactor; 4 . . . stirrer; 6, 8 . . . lines; 10 . . . steam jacket; 12, 14 . . . line for steam; 16 . . . line; 18 . . . pump; 20 . . . hydrocyclone; 22 . . . line (for heavy liquid); 24 . . . line (for light liquid); 26, 28 . . . flow-regulating valve.

EMBODIMENT OF THE INVENTION

Hereafter, an embodiment wherein the present invention is applied to a telomerization reaction of a perfluoroalkyl iodide telomer with tetrafluoroethylene which reaction is catalyzed by copper particles as a catalyst, is described with reference to the drawing.

FIG. 1 shows an apparatus wherein the method for producing a perfluoroalkyl iodide telomer of the present invention is carried out using the method for recovering a catalyst of the present invention.

In FIG. 1, the telomer production apparatus 1 has a reactor 2 wherein the telomerization reaction proceeds, and a catalyst recovery system which has a hydrocyclone 20, a line 16 which delivers a slurry containing a reaction product and the catalyst from reactor 2 to the hydrocyclone 20, and a line 22 which passes a heavy liquid which is obtained from the hydrocyclone 20, to the reactor 2. The reactor 2 includes a stirrer 4. The starting materials are supplied to the reactor 2 via lines 6 and 8. The line 6 is used for supplying tetrafluoroethylene and the line 8 is used for supplying a perfluoroalkyl iodide. The reactor 2 is covered with a jacket 10, and a line 12 for introducing steam and a line 14 for discharging steam are connected to the jacket 10. Steam is used for heating the reactor 2.

As described, the line 16 is connected to the bottom of the reactor 2 for drawing the slurry containing the reaction product and the catalyst and introducing the slurry to the hydrocyclone 20. For drawing the slurry, for example, a pump 18 is used. The line 22 for discharging the heavy liquid and the line 24 for discharging the light liquid are connected to the hydrocyclone 20. The line for heavy liquid 22 is connected to the reactor 2. The catalyst contained in the heavy liquid is recycled to the reactor 2 via the line 22. The line for light liquid 24 is connected to a predetermined apparatus so that the light liquid which contains the reaction product is subjected to the next step. In the illustrated embodiment, flow-regulating valves 26 and 28 are provided for regulating the flow rates of the heavy liquid and the light liquid.

Firstly, a method for producing the perfluoro alkyl iodide telomer by making the telomerization reaction proceed in the reactor is described.

Tetrafluoroethylene as a taxogen and a perfluoroalkyl iodide as a telogen are introduced into the reactor 2 via lines 6 and 8 respectively. Tetrafluoroethylene is a material in a gas phase, and the perfluoroalkyl iodide is a material in a liquid phase.

The catalyst is introduced into the reactor, for example, before initiating the reaction. The catalyst may be introduced together with the perfluoroalkyl iodide (telogen) via line 8. The catalyst is preferably copper particles. When the copper particles are used as the catalyst, the particles preferably have a particle diameter in the range of 0.1 µm to 1 mm, and more preferably in the range of 20 µm to 0.3 mm. When the copper particles do not have a constant particle diameter, each of the particles preferably has a particle diameter in the above-mentioned preferable or more preferable range, and the average of the diameters is preferably in the range of 20 µm to 200 µm, and more preferably in the range of 45 µm to 100 µm. When the copper particles are used as the catalyst, the input amount of the catalyst is selected so that the telomer is obtained in a desired yield. In the case where the catalyst is introduced before the initiation of the reaction, the input amount of the catalyst may be larger than the amount theoretically needed, depending on the degree of deactivation of the recovered catalyst. Further, the catalyst may be optionally replenished depending on the degree of deactivation of the catalyst.

The degree of deactivation of the catalyst recovered by the method for recovering the catalyst of the present invention is small. Therefore, by employing the catalyst recovery method of the present invention, the input amount of the catalyst (that is, the catalyst concentration in the reaction system) can be smaller than that of the catalyst which is to be recovered by a conventional method, when the input amount is selected considering the degree of deactivation of the catalyst. This is the case when the catalyst is replenished depending on the degree of deactivation of the catalyst.

The telomerization reaction may be made progress under conventional condition. The telomerization reaction may be made progress, for example at a reaction temperature between 100° C. and 200° C. and under a reaction pressure between 1.01 MPa and 2.02 MPa (10 atm and 20 atm). The reaction condition is merely one example, and it is selected most economically depending on the characteristic of the catalyst so that the yield of the reaction product can be a desired one.

The telomerization reaction is carried out under the selected condition by stirring the starting material with the stirrer 4 in the reactor 2. By stirring, a slurry wherein the solid copper particles are suspended is formed in the reactor 2. As the residence time of the starting materials in the reactor is longer, the chain length of the telomer molecule tends to be longer. When the residence time of the starting materials in the reactor is shorter, the ratio of the unreacted starting materials in the slurry that is delivered from the reactor to the hydrocyclone is larger. Therefore, the flow rate of the slurry drawn from the reaction system is preferably selected such that the telomer molecule of the desired chain length is obtained and the ratio of the unreacted starting materials is not too large. The starting materials are continuously introduced into the reactor depending on the flow rate of the slurry drawn from the reaction system, so that the fluid level in the reactor can be constant whereby the telomerization reaction proceeds continuously.

Next, a method for separating the catalyst from the slurry drawn from the reaction system and reusing the catalyst is described. The slurry contains the reaction product in a liquid phase and the copper particles in a solid phase, and is delivered to the hydrocyclone. As shown in FIG. 1, the hydrocyclone 20 comprises a cylindrical portion 20a and a conical portion 20b.

The slurry drawn from the reaction system falls inside the hydrocyclone as a spiral flow while the copper particles contained in the slurry are classified.

The high-concentration slurry drawn from the bottom of the hydrocyclone contains a large part of the catalyst contained in the slurry drawn from the reaction system. In the production apparatus as shown in FIG. 1, the high-concentration slurry is returned to the reactor 2 via the line 22 and reused in the reaction system. The flow rate of the high-concentration slurry may be adjusted by the flow-regulating valve 26.

The low-concentration slurry drawn from the top of the hydrocyclone contains the reaction product and the copper particles of a smaller particle diameter. This slurry is subjected to the next step such as a distillation for separating the reaction product from the unreacted starting materials. In that case, the unreacted starting materials may be recycled to the reactor. In the production apparatus as shown in FIG. 1, the low-concentration slurry is delivered via the line 24 to an apparatus for carrying out the next step. The flow rate of the low-concentration slurry may be adjusted by the flow-regulating valve 28.

The embodiment described above is merely one example of the method for producing a perfluoroalkyl iodide telomer of the present invention using the catalyst recovery method of the present invention. There are other various embodiments.

For example, when two kinds of copper particles which differs in particle diameter are used in the telomerization reaction, two hydrocyclones may be used which have different classification points and connected in series. In that case, the copper particles with a larger diameter are recovered by means of the first hydrocyclone, and a slurry which is drawn from the top of the first hydrocyclone and contains copper particles with a small diameter is introduced into the second hydrocyclone for the purpose of recovering the copper particles with a smaller diameter.

Even if the copper particles with a substantially constant diameter is used, the recovery percentage of the copper particles can be increased by using two or more hydrocyclones connected in series. When two or more hydrocyclones are connected in series, the low-concentration slurry drawn from the top of a hydrocyclone is supplied to the next hydrocyclone with which the particles contained in the low-concentration slurry are classified. When the slurry that contains the copper particles with a substantially constant diameter is treated with a plurality of hydrocyclones connected in series, the diameters of the cylindrical portions of the hydrocyclones may be the same, or different from each other.

In the case where the amount per unit time of the slurry drawn from the reaction system is larger than that the amount per unit time which can be treated with one hydrocyclone, the catalyst may be recovered with a plurality of hydrocyclones connected in parallel. In that case, the high-concentration slurry is drawn from the bottom of each hydrocyclone and delivered to the reactor. The high-concentration slurry from the hydrocyclones may be delivered together to the reactor via one line or may be delivered via separate lines. Alternatively, the hydrocyclones are divided into groups each consisting of several hydrocyclones and the high-concentration slurry may be delivered to the reactor through lines each of which is allotted to each group. The low-concentration slurry drawn from the top of each hydrocyclone may be joined into one line followed by being subjected to the next step. Alternatively, the low-concentration slurry drawn from the top of hydrocyclones may be subjected to different steps via different lines. It is possible to use a large reactor by employing a plurality of hydrocyclones in parallel. The use of the large reactor is advantageous in the industrial production of the telomer.

In another embodiment, another centrifugal classifier is substituted for the hydrocyclone. The another centrifugal classifier is, for example, a centrifugal settling machine of cylindrical shape type, separation disc type or decanter type.

The catalyst recovery method of the present invention and the catalyst recovery system of the present invention are described by exemplifying the embodiment which is employed in the production of perfluoroalkyl iodide telomer. The catalyst recovery method of the present invention and the catalyst recovery of the present invention can be applied to other chemical reactions. The chemical reaction to which the catalyst recovery method of the present invention is, for example, a reaction wherein the powder catalyst is dispersed in a liquid phase. Specifically, such a reaction is an alcohol synthesis by the hydrogenation reaction of a ketone or an aldehyde, wherein Pd, Ni or Cu is used as the catalyst.

The catalyst recovery method of the present invention and the catalyst recovery system of the present invention may be combined with other solid-liquid separation method and solid-liquid separation system. The other solid-liquid separation is, for example, filtration by means of a filter, or filtration or sedimentation by means of a centrifugal machine.

The method for producing a perfluoroalkyl iodide telomer of the present invention can be applied to various combinations of telogen and taxogen. The specific combinations to which the present invention can be applied include 2-iodoperfluoropropane/tetrafluoroethylene, 1-iodoperfluoroethane/tetrafluoroetyhlene, 1-iodoperfluorobutane/tetrafluoroethylene, and 1-iodoperfluorohexane/tetrafluoroethylene.

In the method for producing a perfluoroalkyl iodide telomer, the catalyst may be a solid particulate catalyst other than the copper particle or a combination of the copper particle and other solid particulate catalyst. The solid particulate catalysts other than copper particle which are used in the production of a perfluoroalkyl iodide telomer include, for example, Zn, Sn, Mg, V, Rh, Re and Ag particles. The preferable particle diameter and the average of particle diameters are as described in connection with the copper particle.

INDUSTRIAL APPLICABILITY

In each step of the catalyst recovery method of the present invention, the object of each treatment is a slurry which is a fluid, and a slurry is obtained after the treatment. Therefore the recovery method can be continuously carried out. Further, this recovery method makes it possible to recover a catalyst in the form of dense slurry with a constant catalyst content and to recycle it to the reaction system continuously. As a result, the catalyst concentration can be maintained at a constant level in the reaction system, and thereby a chemical reaction can be continued stably for long period of time. Furthermore, the catalyst recovery method of the present invention can reduce the degree of deactivation of the catalyst during the recovery operation, which contributes to the stability of chemical reaction. Therefore, the catalyst recovery method of the present invention can be applied to various chemical reactions which require a catalyst, and is useful for industrial production of chemicals which requires a continues production. Similarly, the catalyst recovery system of the present invention for carrying out the catalyst recovery method of the present invention can be incorporated into various chemical plants and contributes to the production efficiency of chemicals. The method and system for recovering a catalyst of the present invention are suitable for production of a perfluoroalkyl iodide telomer.

The catalyst recovery method of the present invention does not necessarily need to be carried out continuously. A certain amount of slurry may be drawn from the reactor discontinuously, that is, in a batch process.

EXAMPLES

The present invention is described in detail by the following examples.

Example 1: Tests 1 to 4

In Example 1, a relationship between the operation condition of a hydrocyclone and the recovery rate (distribution ratio in a heavy liquid) of a catalyst was studied.

By using a production apparatus 1 as shown in FIG. 1, a telomerization reaction was conducted while recovering a catalyst and recycling the catalyst to a reactor 2. The reactor 2 used in the telomerization reaction had a capacity of 100 litter and was equipped with a stirrer 4. A hydrocyclone 20 used for recovering the catalyst was a hydrocyclone made of ceramic which was manufactured by Japan Chemical Engineering & Machinery Co., Ltd. and had a diameter of about 2.0 cm at the cylindrical portion 20a and an overall height of about 10 cm. In this example, one hydrocyclone 20 was used.

Firstly, 120 kg of $CF_3CF_2I$ as a telogen was charged into the reactor 2 together with 2.4 kg of copper particles (manufactured by Kishida Chemical Co., Ltd.) having the average particle diameter of 46 μm. A slurry in which copper particles were suspended was formed by stirring while the slurry was heated to 110° C. by introducing steam into a steam jacket 10.

Tetrafluoroethylene as a taxogen was introduced into the reactor 2 via a line 6 while maintaining the temperature inside the reactor 2 at 110° C. so that the pressure inside the reactor 2 became 10 MPa. Stirring was further continued for 30 minutes. When the pressure inside the reactor 2 became 9.5 MPa, it was confirmed by gas chromatography that the telomerization in initial state proceeded (that is, a peak of the product appeared in a chart of gas chromatography).

Next, a portion of the slurry was drawn from the bottom of the reactor 2 and delivered to the hydrocytone 20 via a line 16 using a pump 18 while maintaining the temperature and pressure condition. The concentration of catalyst (that is, the concentration of copper particles) in the drawn slurry was about 2% by weight. This slurry was made to fall inside the hydrocyclone 20 so as to classify the copper particles in the slurry. A heavy liquid containing the copper particles with a larger diameter was drawn from the bottom of the hydrocyclone 20 and recycled to the reactor 2 via a line 22. A light liquid containing the copper particles with a smaller diameter was withdrawn from the top of the hydrocyclone 20 via a line 24, and subjected to a distillation step so as to separate a reaction product from unreacted starting materials. The operation condition of the hydrocyclone was set as shown in Table 1 so that the tests were carried out under conditions different from each other.

For each test, the concentrations of the copper particles in the heavy liquid and the light liquid and the distribution ratio of the copper particles were determined. The results are shown in Table 2.

TABLE 1

| | | Test 1 | Test 2 | Test 3 | Test 4 |
|---|---|---|---|---|---|
| Pressure ($\times 10^5$ Pa) | Supplied slurry | 2.02 | 4.04 | 6.06 | 6.06 |
| | Light liquid | 0 | 0.30 | 0.71 | 0 |
| | Heavy liquid | 0 | 0 | 0 | 0 |
| Flow rate (l/hr) | Supplied slurry | 105.1 | 137.7 | 171.2 | 163.3 |
| | Light liquid | 91 | 112.8 | 139.5 | 120.5 |
| | Heavy liquid | 14.1 | 24.9 | 31.7 | 42.8 |
| Ratio of flow rate (%) | Light liquid | 86.6 | 81.9 | 81.5 | 73.8 |
| | Heavy liquid | 13.4 | 18.1 | 18.5 | 26.2 |

TABLE 2

| | | Test 1 | Test 2 | Test 3 | Test 4 |
|---|---|---|---|---|---|
| Concentration of copper particles (wt %) | Light liquid | 0.39 | 0.20 | 0.07 | 0.05 |
| | Heavy liquid | 9.09 | 7.80 | 4.89 | 7.28 |
| Distribution ratio of copper particles (%) | Light liquid | 19.79 | 9.80 | 3.57 | 2.32 |
| | Heavy liquid | 80.21 | 90.20 | 96.43 | 97.68 |

As shown in Table 2, the larger the flow rate of the slurry supplied to the hydrocyclone is so that the flow speed is higher, the larger the distribution ratio of copper particles in the heavy liquid is, resulting in a higher recovery rate of catalyst.

Example 2: Tests 5 and 6

In Example 2, the recovery rate of catalyst (that is, the distribution ratio in heavy liquid) which was achieved with one hydrocyclone was compared with the recovery rate of catalyst which was achieved with two hydrocyclones connected in series.

In Example 2, Test 5 was conducted with a production apparatus which was the same as that used in Example 1. Test 6 was conducted with a production apparatus which was the same as that used in Example 1 except that: an additional hydrocyclone was used; a line was connected between the two hydrocyclones so that a light liquid from the hydrocyclone 20 was introduced into the additional hydrocyclone;

and another line was provided so as to recycle a heavy liquid from the additional hydrocyclone to the reactor.

In each test, 120 kg of CF3CF2I as a telogen was charged into the reactor 2 together with 600 g of copper powder (manufactured by Mitsui Mining and Smelting Co., Ltd.) having the average particle diameter of 52 μm. A slurry in which copper particles were suspended was formed by stirring while the slurry was heated to 110° C. by introducing steam into the steam jacket 10.

Tetrafluoroethylene as a taxogen was introduced into the reactor 2 via the line 4 while maintaining the temperature inside the reactor 2 at 110° C. so that the pressure inside the reactor 2 became 10 MPa. Stirring was further continued for 30 minutes. When the pressure inside the reactor 2 became 9.5 MPa, it was confirmed by gas chromatography that the telomerization in initial state proceeded.

Next, a portion of the slurry was drawn from the bottom of the reactor 2 and delivered to the hydrocyclone via the line 16 using the pump 18 while maintaining the temperature and pressure condition. The concentration of catalyst (that is, the concentration of copper particles) in the drawn slurry was about 0.5% by weight.

In Test 5, the copper particles were classified using a hydrocyclone which was the same as that used in Example 1. The heavy liquid containing the copper particles with a larger diameter resulting from classification was drawn from the bottom of the hydrocyclone 20, and recycled to the reactor 2 via the line 22. The light liquid containing the copper particles with a smaller diameter was drawn from the top of the hydrocyclone 20 via the line 24, and subjected to a distillation step so as to separate a reaction product from unreacted starting materials.

In Test 6, two hydrocyclones each of which was the same as that used in Example 1 were connected in series. The slurry drawn from the reactor was made fall inside the first hydrocyclone. A heavy liquid obtained by this operation was recycled to the reactor, and a light liquid obtained by this operation was delivered to the second hydrocyclone and the copper particles contained in the light liquid were again classified. A heavy liquid obtained in the second hydrocyclone was recycled to the reactor, and a light liquid from the second hydrocyclone was subjected to a distillation step so as to separate a reaction product from unreacted starting materials.

The operation conditions for Tests 5 and 6 were set as shown in Table 3. The operation condition of the first hydrocyclone in Test 6 was the same as that of the hydrocyclone in Test 5.

TABLE 3

|  |  | Test 5 | Test 6 First hydrocyclone | Test 6 Second hydrocyclone |
|---|---|---|---|---|
| Pressure (×10⁵ Pa) | Supplied slurry | 6.06 | 6.06 | 4.04 |
|  | Light liquid | 0 | 0 | 0 |
|  | Heavy liquid | 0 | 0 | 0.51 |
| Flow rate (l/hr) | Supplied slurry | 119.7 | 119.7 | 98.4 |
|  | Light liquid | 71.7 | 71.7 | 66.0 |
|  | Heavy liquid | 48.0 | 48.0 | 32.4 |
| Ratio of flow rate (%) | Light liquid | 59.9 | 59.9 | 67.1 |
|  | Heavy liquid | 40.1 | 40.1 | 32.9 |

For each test, the concentrations of the copper particles in the heavy liquid and the light liquid and the distribution ratio of the copper particles were determined. The results are shown in Table 4. AS to Test 6, the distribution ratio is shown of as the ratio of the copper particles distributed in the light liquid from the second hydrocyclone to the total ratios of the copper particles in the heavy liquids from the first hydrocyclone and the second hydrocyclone.

TABLE 4

|  |  | Test 5 | Test 6 First hydrocyclone | Test 6 Second hydrocyclone |
|---|---|---|---|---|
| Concentration of copper particles (wt ppm) | Light liquid | 67 | 67 | 18 |
|  | Heavy liquid | 8927 | 8927 | 167 |
| Distribution ratio of copper particles (%) | Light liquid | 1.05 |  | 0.19 |
|  | Heavy liquid | 98.95 |  | 99.81 |

As shown in Table 4, when using two hydrocyclones connected in series, the distribution ratio of copper particles in the heavy liquid is higher and the catalyst is recovered at a higher recovery rate, compared with the case of single hydrocyclone.

The invention claimed is:

1. A method for producing a perfluoroalkyl iodide telomer by a telomerization reaction of a perfluoroalkyl iodide with tetrafluoroethylene catalyzed with a solid catalyst containing copper particles, which comprises:

drawing a slurry containing the perfluoroalkyl iodide telomer and the catalyst from a reaction system;

classifying the catalyst in the drawn slurry by a wet-type centrifugal classifier to give a high-concentration slurry having a catalyst weight concentration higher than that of the drawn slurry and a low-concentration slurry having a catalyst weight concentration lower than that of the drawn slurry; and recycling the high-concentration slurry to the reaction system, wherein activity of the catalyst in the high-concentration slurry is higher than the activity of the catalyst in the drawn slurry.

2. The method according to claim 1, wherein the wet-type centrifugal classifier is a hydrocyclone.

3. The method according to claim 2, wherein the catalyst is classified by two or more hydrocyclones which are connected in series.

4. The method according to claim 1, wherein the catalyst is copper particles.

5. The method according to claim 1, wherein 90% by weight of the catalyst is distributed in the high-concentration slurry by classification.

6. The method according to claim 1, wherein the catalyst concentration is constant in the reaction system.

* * * * *